United States Patent [19]

Fodor et al.

[11] Patent Number: 5,378,842
[45] Date of Patent: Jan. 3, 1995

[54] IMIDAZOLIUM HARDENERS FOR PROTEINACEOUS MATERIALS

[75] Inventors: Ludovic Fodor; Richard R. M. Jones, both of Hendersonville; Rolf T. Weberg, Brevard, all of N.C.

[73] Assignee: E. I. Du Pont de Nemours and Company, Wilmington, Del.

[21] Appl. No.: 170,844

[22] Filed: Dec. 21, 1993

[51] Int. Cl.$^6$ ............... C07D 295/104; C07D 233/22; C07D 233/24
[52] U.S. Cl. ........................ 544/139; 548/334.1; 548/316.4; 548/317.1; 548/318.5; 548/323.1; 430/623
[58] Field of Search ............... 548/334.1, 316.4, 317.1, 548/318.5, 323.1; 430/623; 544/139

[56] References Cited

U.S. PATENT DOCUMENTS 3,880,665  4/1975  Himmelmann ............ 96/111
4,063,952 12/1977  Himmelmann et al. ...... 96/111
5,034,249  7/1991  Reif et al. ................ 427/338

FOREIGN PATENT DOCUMENTS 0345514  5/1989  Germany ................ 96/111

OTHER PUBLICATIONS

Lapshin, Kumpan, Komissarov, Cholinomimetic activity of highly stable N-acylonium salts, *Chemical Abstracts*, 116, 16, 1992.
Lapshin, Kumpan, Komissarov, Cholinomimetic activity of highly stable N-acyl carbamoylimidazole onium salts, *Chemical Abstracts*, 115, 64025, 1991.

*Primary Examiner*—Mary C. Lee
*Assistant Examiner*—Joseph K. McKane

[57] ABSTRACT

An improved imidazolium hardener is described. These novel hardeners are specifically advantageous for hardening, or crosslinking, a hydrophilic colloid in a photographic element. The advance in the art is realized in A hardening agent chosen from the set consisting of:

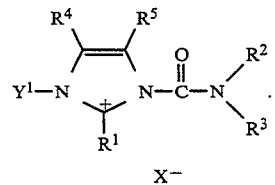

7 Claims, No Drawings

IMIDAZOLIUM HARDENERS FOR PROTEINACEOUS MATERIALS

FIELD OF INVENTION

This invention is related to improved hardeners for proteinaceous materials. More specifically this invention is related to improved imidazolium hardeners for crosslinking a proteinaceous material for use in a photographic film.

BACKGROUND OF THE INVENTION

Proteinaceous materials are used for a wide variety of applications. One of the predominant useful properties is their ability to dissolve in aqueous solutions and yet form a solid matrix which is permeable to aqueous solutions upon drying. These properties have been exploited for many generations in the field of photographic sciences and proteinaceous materials are still widely used as a binder for harbouring silver halide grains in the photosensitive layer of most photographic films.

Formation of a solid matrix is typically considered to be a result of inter-and intra-molecular hydrogen bonding within both the crystalline and amorphous regions of proteinaceous materials. If only the natural hydrogen bonding is employed, the wet strength of the matrix is typically insufficient for use in a photographic film. Therefore, it is common practice to add a crosslinking agent, also known as a hardener, to a protein material when used for photographic layers.

Hardeners are chosen, in part, for their ability to link one group on a protein molecule with another group on the same, or different, protein molecule. The linking generates a three-dimensional network of proteinaceous material. This three-dimensional network has sufficient wet strength to swell during processing without detrimental effects on the silver halide grain harboured therein. Another important aspect of the three-dimensional network is an ability to allow solution to permeate freely during the photographic processing steps of development, fix (or bleach) and wash. It is imperative that the solution which freely permeates the matrix is not stongly absorbed. This is particularly important for photosensitive elements since they must often be capable of transiting the photographic processing steps of development, fix, wash and dry in 20–120 sec.

Two broad classes of hardeners are known in the art. One class reacts with two proteinaceous groups and then becomes an integral part of the resulting bond. Examples of this type of hardener are legion in number and include aldehydes, triazines, chromealum and the like. A second class of hardener is thought to activate one group of a protein molecule, typically a carboxyl group, and thereby facilitate reactivity with a second, typically amine, group of a protein molecule. Reaction with the second group of proteinaceous molecules is typically thought to be a nucleophilic attack which displaces a derivative of the hardener. The resulting bond does not include the hardener but instead is a linkage involving; only chemical elements which were integral to the protein material prior to hardening. This latter type of hardener is typically referred to in the art as a "peptide coupler" since they act to form a peptide bond by fusing existing groups of a protein molecule. The hardener molecules of the present invention are considereds to be in the class of hardeners known as peptide couplers.

Peptide couplers are well known in the art and the examples are legion in number. One particularly advantageous class of peptide couplers is the 1,3-bis-carbamoyl imidazolium compounds described in U.S. patent application Ser. No. 07/817,692 filed Jan. 7, 1992. The 1,3-bis-carbamoyl imidazolium compounds offer several advantages over previous hardeners. Particularly advantagous is their solubility in aqueous solution, their stability towards decomposition, and their ability to react in a time frame which is convenient for coating and drying gelatin.

While 1,3-bis-carbamoyl imidazolium compounds are advantageous over previously known hardeners there is still a need to improve the art of hydrophilic colloid hardening. One aspect of the 1,3-bis-carbamoyl imidazolium compounds which is particularly troublesome is the synthetic procedure. The reaction involves the use of two equivalents of carbamoyl chloride derivatives. Many carbamoyl chloride derivatives are known carcinogens. One skilled in the art of chemical sciences would realize the advantage of reducing, or eliminating, the need to use such compounds in an industrial chemical environment.

Yet another disadvantage with available imidazolium couplers is the high level of water absorption of the resulting crosslinked film. As mentioned previously, excess water absorption is detrimental to a photographic element and it is important that water absorption to the matrix remain low while at the same time allowing the processing solutions to permeate freely. There is an ongoing need in the art for a hardener which affords lower water absorption properties. At the same time, this decreased water absorption must be accomplished without compromising other properties such as permeability, strength and the like.

SUMMARY OF THE INVENTION

It is an object of the present invention to provide an improved hardener for a hydrophilic colloid.

It is another object of the present invention to provide a hardener which affords lower water absorption of a hydrophilic colloid without loss of strength as measured by the melting point of the coating.

It is another object of the present invention to provide a hardener which can be incorporated into a polymer.

A particular feature of an embodiment of the present invention is the ability to act as a surfactant and a hardener.

These advantages, and others as will be apparent from the teachings herein, are provided in a compound suitable as a hardening agent chosen from the set consisting of:

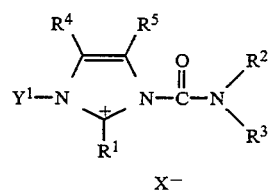

wherein:
$Y^1$ represents an alkyl of 6–24 carbons, aryl of 6–24 carbons, aralkyl of 7 to 25 carbons, the atoms chosen from C, N, O, and S necessary to form a 5- or 6-membered ring. or -$L^1CR^{13}CH_2$;

L¹ is a linking group;
R¹ is hydrogen, alkyl of 1 to 24 carbons, aryl of 6 to 24 carbons, aralkyl of 7 to 25 carbons or halogen;
R² and R3 independently represent alkyl of 1–24 carbons, aryl of 6–24 carbons, aralkyl of 7 to 25 carbons or R² and R³ independently may represent, or be taken together to represent the atoms chosen from C, N, O and S necessary to form a 5- or 6-membered ring;
R⁴ and R5 independently represent hydrogen, alkyl of 1 to 24 carbons, nitro, carboxyl, mercapto, —OR¹¹, or the atoms chosen from C, N, O and S necessary to form a 5- or 6-membered ring or R⁴ and R⁵ may be taken together to represent the atoms chosen from C, N, O and S necessary to form a 5- or 6-membered ring;
R¹¹ represents hydrogen or an alkyl of 1–5 carbons;
R¹³ represents hydrogen or an alkyl of 1–24 carbons;
X- is a counterion; and

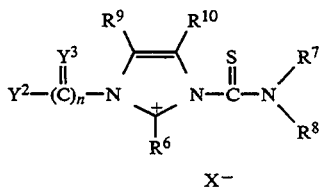

wherein:
Y² is an alkyl of 1–24 carbons, aryl of 6–24 carbons, aralkyl of 7 to 25 carbons, the atoms chosen from C, N, O and S necessary to from a 5or 6-membered ring or L²CR¹⁴CH₂;
L² is a linking group;
Y³ represents O or S;
R⁶ is hydrogen, alkyl of 1 to 24 carbons, aryl of 6 to 24 carbons, aralkyl of 7 to 25 carbons or halogen;
R⁷ and R⁸ independently represent alkyl of 1–24 carbons, aryl of 6–24 carbons, aralkyl of 7 to 25 carbons or the atoms chosen from C, N, O and S necessary to form a 5- or 6-membered ring or R⁷ and R⁸ may be taken together to represent the atoms C, N, O and S necessary to form a 5- or 6-membered ring;
R⁹ and R¹⁰ independently represent hydrogen, alkyl of 1 to 24 carbons, nitro, carboxyl, mercapto, —OR¹², the atoms chosen from C, N, O, and S necessary to form a 5- or 6-membered ring or taken together R⁹ and R¹⁰ may represent the atoms chosen from C, N, O, and S necessary to form a 5- or 6-membered ring;
R¹² represents hydrogen or an alkyl of 1–5 carbons;
R¹⁴ represents hydrogen or an alkyl of 1–24 carbons;
X- is a counterion;
n is an integer chosen from 0 and 1.
A particularly preferred embodiment is provided in a hardening agent chosen from the set consisting of:

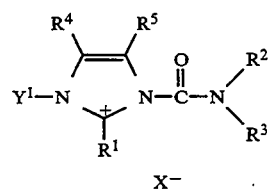

wherein:

Y¹ represents an aryl of 1–24 carbons, aralkyl of 7 to 25 carbons, the atoms chosen from C, N, O, and S necessary to form a 5- or 6-membered ring, or -L¹CR¹³CH₂;
L¹ is a linking group;
R¹ is hydrogen, alkyl of 1 to 24 carbons, aryl of 6 to 24 carbons, aralkyl of 7 to 25 carbons or halogen;
R² and R³ independently represent alkyl of 1–24 carbons, aryl of 6–24 carbons, aralkyl of 7 to 25 carbons or R² and R³ independently may represent, or be taken together to represent the atoms chosen from C, N, O and S necessary to form a five or six membered ring;
R⁴ and R⁵ independently represent hydrogen, alkyl of 1 to 24 carbons, nitro, carboxyl, mercapto, —OR¹¹, or the atoms chosen from C, N, O, and S necessary to form a 5- or 6-membered ring or R⁴ and R⁵ may be taken together to represent the atoms chosen from C, N, O, and S necessary to form a 5- or 6-membered ring;
R¹¹ represents hydrogen or an alkyl of 1–5 carbons;
R¹³ represents hydrogen or an alkyl of 1–24 carbons;
X- is a counterion;
with the proviso that at least one substituent chosen from the set consisting of Y¹, R¹, R², R³, R⁴ and R⁵ represents an alkyl of 6–24 carbons; and

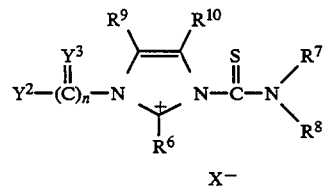

wherein:
Y² is an alkyl of 1–24 carbons, aryl of 6–24 carbons, aralkyl of 7 to 25 carbons, the atoms chosen from C, N, O, and S necessary to form a 5- or 6-membered ring,L²CR¹⁴CH₂;
L² is a linking group;
Y³ represents O or S;
R⁶ is hydrogen, alkyl of 1 to 24 carbons, aryl of 6 to 24 carbons, aralkyl of 7 to 25 carbons or halogen;
R⁷ and R⁸ independently represent alkyl of 1–24 carbons, aryl of 6–24 carbons, aralkyl of 7 to 25 carbons or the atoms chosen from C, N, O and S necessary to form a 5- or 6-membered ring or R⁷ and R⁸ may be taken together to represent,: the atoms chosen from C, N, O and S necessary to form a 5- or 6-membered ring;
R⁹ and R¹⁰ independently represent hydrogen, alkyl of 1 to 24 carbons, nitro, carboxyl, mercapto, —OR¹², the atoms chosen from C, N, O, and S necessary to form. a 5- or 6-membered ring or taken together R⁹ and R¹⁰ may represent the atoms chosen from C, N, O, and S necessary to form a 5- or 6-membered ring;
R¹² represents hydrogen or an alkyl of 1–5 carbons;
R14 represents hydrogen or an alkyl of 1–24 carbons;
X- is a counterion;
n is an integer chosen from 0 and 1.
A particularly preferred application is realized when the hardener is used in a hydrophilic colloid layer as provided in a photographic element comprising at least one hydrophilic colloid layer wherein at least one said hydrophilic colloid layer is hardened with a compound chosen from the set consisting of:

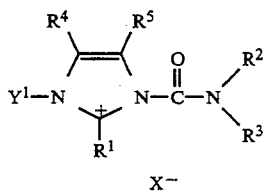

wherein:
$Y^1$ represents an alkyl of 6–24 carbons, aryl of 6–24 carbons, aralkyl of 7 to 25 carbons, the atoms chosen from C, N, O, and S necessary to form a 5- or 6-membered ring, $-L^1CR^{13}CH_2$;
$L^1$ is a linking group;
$R^1$ is hydrogen, alkyl of 1 to 24 carbons, aryl of 6 to 24 carbons, aralkyl of 7 to 25 carbons or halogen;
$R^2$ and $R^3$ independently represent alkyl of 1–24 carbons, aryl of 6–24 carbons, aralkyl of 7 to 25 carbons or $R^2$ and $R^3$ independently may represent, or be taken together to represent the atoms chosen from C, N, O and S necessary to form a 5- or 6-membered ring;
$R^4$ and $R^5$ independently represent hydrogen, alkyl of 1 to 24 carbons, nitro, carboxyl, mercapto, $-OR^{11}$, or the atoms chosen from C, N, O, and S necessary to form a 5- or 6-membered ring or $R^4$ and $R^5$ may be taken together to represent the atoms chosen from C, N, O, and S necessary to form a 5- or 6-membered ring;
$R^{11}$ represents hydrogen or an alkyl of 1–5 carbons;
$R^{13}$ represents hydrogen or an alkyl of 1–24 carbons;
X- is a counterion;
and

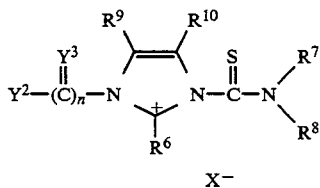

wherein:
$Y^2$ is an alkyl of 1–24 carbons, aryl of 6–24 carbons, aralkyl of 7 to 25 carbons, the atoms chosen from C, N, O, and S necessary to form a 5- or 6-membered ring, $L^2CR^{14}CH_2$;
$L^2$ is a linking group;
$Y^3$ represents O or S;
$R^6$ is hydrogen, alkyl of 1 to 24 carbons, aryl of 6 to 24 carbons, aralkyl of 7 to 25 carbons or halogen;
$R^7$ and $R^8$ independently represent alkyl of 1–24 carbons, aryl of 6–24 carbons, aralkyl of 7 to 25 carbons or the atoms chosen from C, N, O and S necessary to form a 5- or 6-membered ring or $R^7$ and $R^8$ may be taken together to represent the atoms chosen from C, N, O and S necessary to form a 5- or 6-membered ring;
$R^9$ and $R^{10}$ independently represent hydrogen, alkyl of 1 to 24 carbons, nitro, carboxyl, mercapto, $-OR^{12}$, the atoms chosen from C, N, O, and S necessary to form a 5- or 6-membered ring or taken together $R^9$ and $R^{10}$ may represent the atoms chosen from C, N, O, and S necessary to form a 5- or 6-membered ring;
$R^{12}$ represents hydrogen or an alkyl of 1–5 carbons;
$R^{14}$ represents hydrogen or an alkyl of 1–24 carbons;
X- is a counterion;
n is an integer chosen from O and 1.

DETAILED DESCRIPTION OF THE INVENTION

Hardeners of the present invention are represented by Formula I or Formula II.

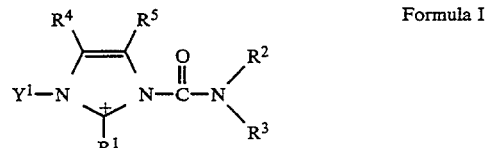

Formula I

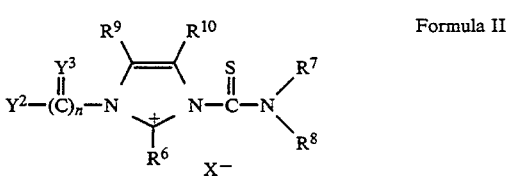

Formula II

Referring specifically to Formula I, $Y^1$ is an alkyl of 6–24 carbons, aryl of 6–24 carbons, aralkyl of 7 to 25 carbons, the atoms chosen from C, N, O, and S necessary to form a 5- or 6-membered ring, $L^1CR^{13}CH_2$, or a polymer thereof, where $L^1$ is a linking group. $L^1$ preferably represents a covalent chemical bond, alkyl of 1 to 20 carbons, aryl of 6–24 carbons, or aralkyl of 7 to 25 carbons. Most preferably $L^1$ represents a covalent chemical bond or an alkyl of 1–3 carbons. $R^{13}$ a hydrogen or an alkyl of 1 to 24 carbons, preferably $R^{13}$ is hydrogen or a methyl. $R^1$ is hydrogen, alkyl of 1 to 24 carbons, aryl of 6 to 24 carbons, aralkyl of 7 to 25 carbons or halogen. Preferably $R^1$ represents hydrogen, alkyl of 1–3 carbons, aryl of 6–10 carbons, or aralkyl of 7–11 carbons. Most preferably $R^1$ represents hydrogen or alkyl of 1–3 carbons. $R^2$ and $R^3$ independently represent alkyl of 1–24 carbons, aryl of 6–24 carbons, aralkyl of 7 to 25 carbons. $R^2$ and $R^3$ independently may represent, or be taken together to represent the atoms chosen from C, N, O and S necessary to form a 5- or 6-membered ring. Preferably $R^2$ and $R^3$ independently represent alkyl of 1–6 carbons, aryl of 6–10 carbons, aralkyl of 7–11 carbons, or taken together $R^2$ and $R^3$ may represent the atoms chosen from C, N and O necessary to form a 5- or 6-membered ring. Most preferably $R^2$ and $R^3$ represent alkyl of 1–3 carbons, or taken together $R^2$ and $R^3$ may represent the atoms chosen from C, N and O necessary to form a 5- or 6-membered ring. $R^4$, and $R^5$ independently represent hydrogen, alkyl of 1 to 24 carbons, nitro, carboxyl, mercapto, $-OR^{11}$, where $R^{11}$ represents hydrogen or an alkyl of 1–5 carbons, $R^4$ and $R^5$ independently may represent the atoms chosen from C, N, O, and S necessary to form a 5- or 6-membered ring or $R^4$ and $R^5$ may be taken together to represent the atoms chosen from C, N, O, and S necessary to form a 5- or 6-membered ring. Preferably $R^4$ and $R^5$ independently represent hydrogen or alkyl of 1–4 carbon atoms. X- is a counterion preferably chosen from the set consisting of halide, $ClO_4$-, $BF_4$-, $p-CH_3C_6H_4SO_3$-.

It is also preferable to incorporate a surfactant moiety into the hardener compound referred to as Formula I.

In this embodiment $Y^1$ can be an alkyl of 1–24 carbons, with the proviso that at least one of the substituents chosen frown the group consisting of $Y^1$, $R^1$, $R^2$, $R^3$, $R^4$ and $R^5$ represents an alkyl of 6–24 carbons.

Referring specifically to Formula II. $Y^2$ is an alkyl of 1–24 carbons, aryl of 6–24 carbons, aralkyl of 7 to 25 carbons, the atoms chosen from C, N, O, and S necessary to form a 5- or 6-membered ring, $L^2CR^{14}CH_2$ or a polymer thereof. $L^2$ is a linking group preferably chosen from the set consisting of a covalent chemical bond, alkyl of 1 to 20 carbons, and aryl of 6–24 carbons. Most preferably $L^2$ represents a covalent chemical bond or an alkyl of 1–3 carbons. $R^{14}$ is a hydrogen or an alkyl of 1–24 carbons, most preferably $R^{14}$ is a hydrogen or methyl. $Y^3$ represents O or S. $R^6$ is hydrogen, alkyl of 1 to 24 carbons, aryl of 6 to 24 carbons, aralkyl of 7 to 25 carbons or halogen. Preferably $R^6$ represents hydrogen, alkyl of 1–3 carbons, aryl of 6–10 carbons, or aralkyl of 7–11 carbons. Most preferably $R^6$ represents hydrogen or alkyl of 1–3 carbons. $R^7$ and $R^8$ independently represent alkyl of 1–24 carbons, aryl of 6–24 carbons, aralkyl of 7 to 25 carbons. $RA^7$ and $R^8$ independently may represent or be taken together to represent the atoms chosen from C, N, O and S necessary to form a 5- or 6-membered ring. Preferably $R^7$ and $R^8$ independently represent alkyl of 1–6 carbons, aryl of 6–10 carbons, aralkyl of 7–11 carbons, or taken together $R^7$ and $R^8$ may represent the atoms chosen from C, N and O necessary to form a 5- or 6-membered ring. Most preferably $R^7$ and $R^8$ represent alkyl of 1–3 carbons, or taken together $R^7$ and $R^8$ may represent the atoms chosen from C, N and O necessary to form a 5- or 6-membered ring. $R^9$ and $R^{10}$ independently represent hydrogen, alkyl of 1 to 24 carbons, nitro, carboxyl, mercapto, $-OR^{12}$ where $R^{12}$ represents hydrogen or an alkyl of 1–5 carbons, $R^9$ and $R^{10}$ may independently represent the atoms chosen from C, N, O, and S necessary to form a 5- or 6-membered ring or taken together $R^9$ and $R^{10}$ may represent the atoms chosen from C, N, O, and S necessary to form a 5- or 6-membered ring. Preferably $R^9$ and $R^{10}$ independently represent hydrogen or alkyl of 1–4 carbon atoms. X- is a counterion preferably chosen from the set consisting of halide, $ClO_4$-, $BF_4$-, p-$CH_3C_6H_4SO_3$-; n is an integer chosen from 0 and 1.

A preferred embodiment of the hardener represented by Formula II is obtained when the compound further incorporates a surfactant moiety. A most preferred hardener is obtained when at least one substituent chosen from the group consisting of $Y_2$, $R^6$, $R^7$, $R^8$, $R^9$ and $R^{10}$ represents an alkyl of 6–24 carbons. Consistent with terminology used in the art, the compound represented by:

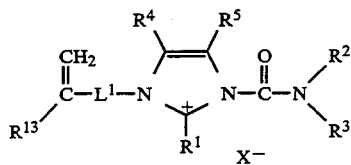

Is a "vinyl imidazolium derivative". The vinyl group of the vinyl imidazolium derivative can be polymerized as known in the art to form a polymer. Preferably the vinyl group of the vinyl imidazolium derivative can be polymerized with other substituted vinyl compounds to form a copolymer. Preferably the vinyl imidazole derivative is a copolymer defined by:

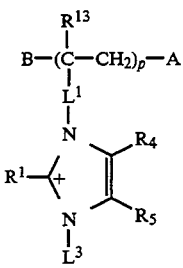

where $L^3$ represents:

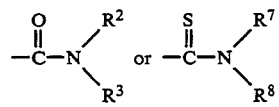

where $R^1$, $R^2$, $R^3$, $R^4$, $R^5$, $R^7$, $R^8$, $R^{13}$ and $L^1$ correspond to the definition above for similarly referenced groups. The subscript p represents the mole fraction of vinyl imidazolium monomer in the polymer and is preferably no more than 50%. A and B independently represent copolymerized monomers. Monomers A and B are preferably chosen from the set consisting of acrylic acid ester, methacrylic acid ester, acrylamide, styrene, styrene sulfonate, maleic anhydride, butadiene and vinyl chloride.

Throughout this disclosure the group $CH_2=CR-$ refers to the unpolymerized monomer. A polymer or copolymer formed by the polymerization or copolymerization of the vinyl group is also considered to be within the teachings of the present invention. The process of polymerization, or copolymerization, is well known in the art and includes specifically radical initiated polymerization.

The recitation "atoms chosen from C, N, O, and S necessary to from a 5- or 6-membered ring" or the equivalent thereof, refers to substituted or unsubstituted rings. Aromatic and aliphatic rings are anticipated as are the rings including but not limited to: the thiazole series; e.g. thiazole, 4-methylthiazole, 4-phenylthiazole, 5-methylthiazole, 5-phenylthiazole, 4,5-dimethylthiazole, 4,5-diphenylthiazole, 4-(2-thienyl)-thiazole;

the benzothiazole series; e.g., benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 4-phenylbenzothiazole, 5-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, tetrahydrobenzothiazole, 5,6-dimethoxybenzothiazole, 5,6-dioxymethylenebenzothiazole, 5-hydroxybenzothiazole, 6-hydroxybenzothiazole;

the naphthothiazole series; e.g., naphtho[1,2]thiazole, naphtho[2,1]thiazole, 5-methoxynaphtho-[2,1]thiazole, 5-ethoxynaphtho[2,1]thiazole, 8-methoxynaphtho[1,2]thiazole, 7-methoxynaphtho[1,2]thiazole;

the thianaphtheno-7',6',4,5-thiazole series; e.g. 4'methoxythianaphtheno-7',6',4,5,thiazole;

the oxazole series; e.g., 4-methyloxazole, 5-methyloxazole, 4-phenyloxazole, 4,5-diphenyloxazole, 4-ethyloxazole, 4,5-dimethyloxazole, 5-phenyloxazole;

the benzoxazole series; e.g., benzoxazole, 5-chlorobenzoxazole, 5-methylbenzoxazole, 5-phenylbenzoazole, 6-methylbenzoxazole, 5,6-dimethylbenzoxazole, 4,5-dimethylbenzoxazole, 5-methoxybenzoxazole, 5-ethoxybenzoxazole, 5-chlorobenzoxazole, 6-methoxybenzoxazole, 5-hydroxybenzoxazole, 6-hydroxybenzoxazole;

the naphthoxazole series, e.g., naphtho[1,2]oxazole, naphtho[2,1]oxazole;

the thiazoline series; e.g., thiazoline, 4-methylthiazoline;

the 2-quinoline series; e.g., quinoline, 3-methylquinoline, 5-methylquinoline, 7-methylquinoline, 8-methylquinoline, 6-chloroquinoline, 8-chloroquinoline, 6-methoxyquinoline, 6-ethoxyquinoline, 6-hydroxyquinoline, 8-hydroxyquinoline;

the 4-quinoline series; e.g., quinoline, 6-methoxyquinoline, 7-methoxyquinoline, 7-methylquinoline, 8-methylquinoline;

the 1-isoquinoline series; e.g., isoquinoline, 3,4-dihydroisoquinoline;

the 3-isoquinoline series; e.g., isoquinoline;

the benzimidazole series; e.g., 1,3-diethylbenzimidazole, 1-ethyl-3-phenylbenzimidazole;

the 3,3-dialkylindolenine series; e.g., 3,3-dimethylindoline, 3,3,5-trimethylindolenine, 3,3,7-trimethylindolenine;

the 2-pyridine series; e.g., pyridine, 5-methylpyridine; and the 4-pyridine series; e.g., pyridine;

the 3,3-dialkylbenz[e]indole series; e.g., 3,3-dimethylbenz[e]indole;

the tetrazole series: e.g., 1-phenyltetrazole, 1-methyltetrazole;

the triazine series: e.g., dichlorotriazine;

the triazole series: e.g., 1-phenyl-triazole, 1-methyl-triazole;

the pyrimidine series: e.g., pyrimidine;

the thiadiazole series: e.g., 1,3,4-thiadiazole.

The terms "alkyl", "aryl", and "aralkyl" and other groups refer to both unsubstituted and substituted groups unless specified to the contrary. Preferred substituents include halogen, nitro, carboxyl, hydroxyl, alkoxy, amine, thiol, amide, vinyl, sulfate, cyano, and thioether.

Well known to the art is the advantage of using a surfactant to assist in coating a solution. Typically the surfactant is a separate entity which is useful during coating and may be detrimental after coating is complete. A preferred embodiment of the present invention is realized when a surfactant moiety is incorporated into the chemical structure of the hardener. This allows a single compound to accomplish multiple task, namely, act as a coating aid during the coating process after which they act to crosslink the matrix as detailed above. Surfactant moieties which are known in the art include alkyls chains over 6 carbons, preferably 6-24 carbons; polyalkyleneoxide chains such as —($R^{15}O)_m$—, wherein $R^{15}$ is ethylenyl, propylenyl or combinations thereof and m is 1-30; or combinations of alkyls, and polyalkyleneoxides.

While not limited thereto, particularly preferred hardeners are represented by:

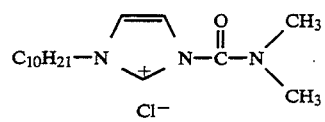

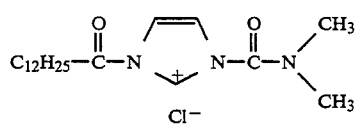

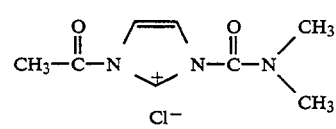

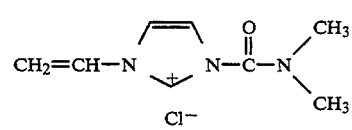

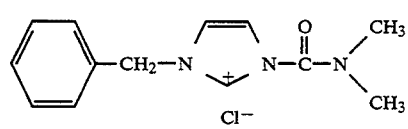

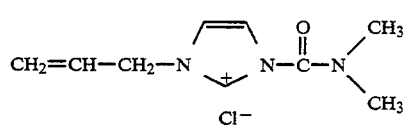

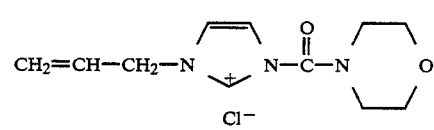

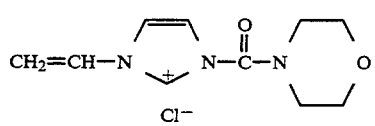

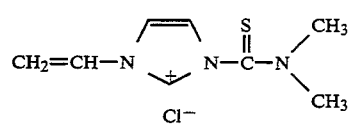

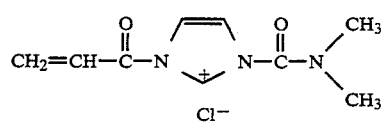

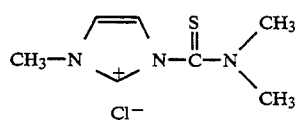

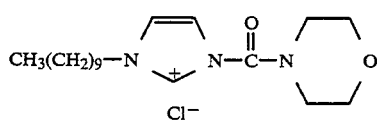

The structure of the imidazolium ring is known to exist with a delocalized charge. Comparable resonance structures can be drawn including:

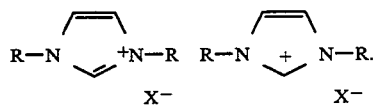

The hardeners of the present invention react rapidly with a hydrophilic colloid and therefore addition of the hardener to a solution containing hydrophilic colloid must be done with care. In a practical sense the addition is typically done just prior to application of the hydrophilic colloid by injection of the hardener into the hydrophilic colloid solution or some similar manner. Preferably, the hardener is dissolved in a suitable solvent such as water, alcohol, dimethylsulfoxide and the like.

The amount of hardener solution added depends on the degree of crosslinking desired. For use in a photographic emulsion the hardener solution is typically added in an amount sufficient to equal 0.01 to 1.0 mmoles of hardener per gram of hydrophilic colloid. More preferred is an amount of 0.2 to 0.30 mmoles of hardener per gram of hydrophilic colloid. The amount added may be different for different hydrophilic colloids.

The hardeners of the present invention are most suitable for crosslinking a hydrophilic colloid layer. It is most preferred to use the hardeners of the present invention for a coated layer of hydrophilic colloid. The commercial application includes, but is not limited to, the use of a hardened hydrophilic colloid layer in a photographic element as either a photosensitive layer, an underlayer, an overcoat layer or a dyed layer.

A photosensitive layer typically comprises silver halide dispersed in a hydrophilic colloid binder. The silver halide is optionally chemically and optionally spectrally sensitized as known in the art and the layer may contain other adjuvants such as dyes, stabilizers, development agents, color coupling agents, toners, surfactants, and the like.

An underlayer typically comprises a hydrophilic colloid layer with an optional dye dispersed therein. The overcoat is typically coated supra to the photosensitive layer as protection from abrasion and the like and may comprise dyes, additional surfactants, or other adjuvants as known in the art.

The term "hydrophilic colloid" or its homologues "gelatin" and "protein" are used herein to refer to the protein substances which are derived from collagen. In the context of the present invention "hydrophilic colloid" also refers to substantially equivalent substances such as synthetic analogues of gelatin. Generally gelatin is classified as alkaline gelatin, acidic gelatin or enzymatic gelatin. Alkaline gelatin is obtained from the treatment of collagen with a base such as calcium hydroxide, for example. Acidic gelatin is that which is obtained from the treatment of collagen in acid such as, for example, hydrochloric acid; and enzymatic gelatin is generated with a hydrolase treatment of collagen. The teachings of the present invention are not restricted to gelatin type or the molecular weight of the gelatin.

The film support for the emulsion layers used in the novel process may be any suitable transparent plastic. For example, the cellulosic supports, e.g. cellulose acetate, cellulose triacetate, cellulose mixed esters, etc. may be used. Polymerized vinyl compounds, e.g., copolymerized vinyl acetate and vinyl chloride, polystyrene, and polymerized acrylates may also be mentioned. Preferred films include those formed from the polyesterification product of a dicarboxylic acid and a dihydric alcohol made according to the teachings of Alles, U.S. Pat. No. 2,779,684 and the patents referred to in the specification thereof. Other suitable supports are the polyethylene terephthalate/isophthalates of British Patent 766,290 and Canadian Patent 562,672 and those obtainable by condensing terephthalic acid and dimethyl terephthalate with propylene glycol, diethylene glycol, tetramethylene glycol or cyclohexane 1,4-dimethanol (hexahydro-pxylene alcohol). The films of Bauer et al., U.S. Pat. No. 3,052,543 may also be used. The above polyester films are particularly suitable because of their dimensional stability.

Meltpoint was measured by observing the melting temperature in 0.1M NaOH for a hardened gelatin coating. Water absorption was determined by weighing a dry 10×10 cm film sample, submerging the sample for 30 minutes in an aqueous solution buffered to a pH of approximately 10.0 by a borate buffer, allowing the excess water on the surface to drain off of the film, and weighing the swollen film. Water absorption (WA) was then defined as $$WA(mg/cm^2) = \frac{\text{Wet weight} - \text{Dry weight (mg)}}{\text{Dry Weight}} \times 100$$

Synthesis of Inventive Hardeners

Standard organic reaction synthetic procedures can be employed as known in the art. While other synthetic procedures may be employed, the inventive hardeners are prepared in a consistent manner according to the following procedure. The appropriate N-substituted imidazole (0.2 mol) and the appropriate carbamyl chloride, carbonyl chloride, thiocarbonyl chloride or thiocarbamyl chloride, (0.2 mol) are dissolved in approximately 100 ml. of acetone and refluxed for approximately 2 hrs. The reaction mixture is cooled to precipate the product which is then recovered by filtration. The precipitate is rinsed with acetone and dried in a dessicator at ambient conditions. A representative synthesis is provided for 1-decyl-3-dimethylcarbamoylimidazolium bromide (I-1).

Synthesis of 1-decyl-3-dimethylcarbamoylimidazolium bromide

To 13.6 gm (0.2 mole) of imidazole (Aldrich Chemical Co., Milwaukee, Wis. 99%) and 20.2 gm of triethylamine (Aldrich, 99%) in 100 ml dry acetone (Fisher Scientific Co., Pittsburgh, Pa.) in a magnetically stirred 250 ml round bottom flask under dry nitrogen was added 21.5 gm (0.2 mole) dimethylcarbamyl chloride (Aldrich, 99%) dropwise over a 20 min. period from a side-arm pressure equalizing addition funnel. A white precipitate formed during the addition under conditions of mild exothermicity. The addition funnel was replaced with a reflux condensor and the reaction refluxed for a further one hour. After cooling to room temperature, the precipitate was isolated by Buchner filtration onto Wattman #1 paper, rinsed on the filter with acetone, and discarded. The combined flitrate and rinse acetone solution was divided into two equal parts, each containing 0.1 mole of 1-dimethylcarbamoylimidazole. To one of these parts was added 22.1 gm (0.1 mole) of 1-bromodecane (Aldrich 98%) and the solution refluxed for seven hours under dry nitrogen. The acetone was evaporated at water aspirator vacuum in a rotoevaporator to the point where two layers formed. The upper layer contained largely unreacted bromodecane and the lower yielded 12 gm (0.043 mole for a 21.4% theorical yield) of the imidazolium salt as a waxy solid upon cooling to 5 C. The purity and identity of this product was confirmed by proton and carbon NMR in deuterium oxide solution.

The hardeners of the present invention were tested versus the comparative hardeners listed below:

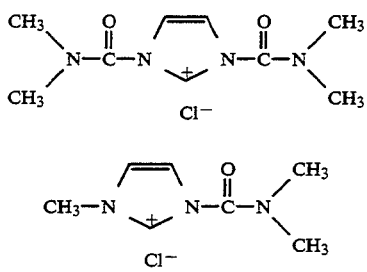

Hardening Examples

The hardener to be tested was added to a gelatin solution comprising 8% standard lime bone gelatin, by weight, and enough surfactant for effective coating with a #40 Mayer rod. The solution is then coated on a polyethylene terephthalate support with a resin coating thereon. The coated solution is allowed to dry for 24 hrs after which the melting properties and water absorption properties are measured. Representative results are contained in Table 1.

TABLE 1

Physical Properties of Gelatin Layer Crosslinked with Inventive Hardeners

| Hardener | Grams of Hardener Gram of Gelatin | Melt Point | WA |
|---|---|---|---|
| C-1 | 0.0125 | 71 | 19.5 |
| C-1 | 0.0250 | 85+ | 17.3 |
| C-1 | 0.0375 | 85+ | 16 |
| I-1 | 0.0212 | 35 | 16.5 |
| I-1 | 0.0425 | 35 | 15.1 |
| I-1 | 0.0637 | 38 | 13.5 |
| I-1 | 0.0848 | 40 | 12.3 |
| I-4 | 0.0125 | 79 | 16.8 |
| I-4 | 0.0250 | 85+ | 14.2 |
| I-4 | 0.0375 | 85+ | 13.8 |
| I-4 | 0.0500 | 85+ | 12.2 |
| I-12 | 0.0125 | 62 | 17.2 |
| I-12 | 0.0250 | 85+ | 16.7 |
| I-12 | 0.0500 | 85+ | 15.8 |

The data in Table 1 indicates that hardening can still be obtained yet the water absorption is lower at equivalent levels of hardener.

Examples of Hardener/Surfactant Compounds

A 10% solution of the compound to be tested was prepared in deionized water to prepare a stock solution. Aliquots of the stock solution were then diluted to the concentrations indicated in Table 2. The surface tension (ST) of the diluted aliquots were measured using a Fisher Surface Tensiomat Model 21 (Fisher Scientific Co., Pittsburgh, Pa.) by the du Nouy ring method with a platinum-iridium ring (6.00 cm mean circumference, R/r=53.748890) at 23° C., pH 5.8, calibrated to benzyl alcohol (39.0 dynes/cm) and deionized water (71.8 dynes/cm). The uncorrected surface tensions are listed in Table 2 wherein concentration is recorded in % by weight and Surface Tension is measured in dynes/cm.

TABLE 2

| Hardener | Surface Tensions Concentration | Surface Tension |
|---|---|---|
| C-2 | 10.0 | 71.6 |
| C-2 | 1.0 | 72.2 |
| C-2 | 0.1 | 71.9 |
| C-2 | 0.01 | 71.8 |
| C-2 | 0.001 | 71.7 |
| C-2 | 0.0001 | 71.1 |
| I-1 | 10.0 | 25.1 |
| I-1 | 1.0 | 25.5 |
| I-1 | 0.5 | 25.6 |
| I-1 | 0.2 | 34.1 |
| I-1 | 0.1 | 40.8 |
| I-1 | 0.05 | 48.5 |
| I-1 | 0.02 | 58.9 |
| I-1 | 0.01 | 63.4 |
| I-1 | 0.001 | 69.9 |
| I-1 | 0.0001 | 72.2 |

The data in Table 2 shows a typical surfactant response for inventive compound I-1 which has a determined critical micelle concentration at or near 0.4 wt % or $1.4 \times 10^{-4}$ molar by the method described in M. J. Rosen, Surfactants and Interfacial Phenomena, J. Wiley and Sons, New York, N.Y., 1978. By comparison, the surface tension response of C-2 indicates only a slight rise typical of many highly ionized salts and contrary to that expected of surfactant activity. By extrapolation, the surfactant effect is expected to be observed when the alkyl group in similar derivatives comprises approximately at least six carbons.

We claim:

1. A compound suitable as a hardening agent chosen from the set consisting of:

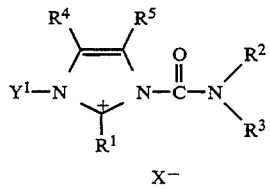

wherein:

$Y^1$ represents an alkyl of 6–24 carbons, aryl of 6–24 carbons, aralkyl of 7 to 25 carbons, the atoms chosen from C, N, O, and S necessary to form a 5- or 6-membered ring, or $-L^1CR^{13}CH_2$;

$L^1$ is a linking group;

$R^1$ is hydrogen, alkyl of 1 to 24 carbons, aryl of 6 to 24 carbons, aralkyl of 7 to 25 carbons or halogen;

$R^2$ and $R^3$ independently represent alkyl of 1–24 carbons, aryl of 6–24 carbons, aralkyl of 7 to 25 carbons or $R^2$ and $R^3$ independently may represent, or be taken together to represent the atoms chosen from C, N, O and S necessary to form a 5- or 6-membered ring;

$R^4$ and $R^5$ independently represent hydrogen, alkyl of 1 to 24 carbons, nitro, carboxyl, mercapto, $-OR^{11}$, or the atoms chosen from C, N, O, and S necessary to form a 5- or 6-membered ring or $R^4$ and $R^5$ may be taken together to represent the atoms chosen from C, N, O, and S necessary to form a 5- or 6-membered ring;

$R^{11}$ represents hydrogen or an alkyl of 1–5 carbons;

$R^{13}$ represents hydrogen or an alkyl of 1–24 carbons;

X- is a counterion;
and $$\begin{array}{c} R^9 \quad R^{10} \\ Y^3 \\ \parallel \\ Y^2-(C)_n-N \underset{\underset{R^6}{\overset{+}{\diagup}}}{\diagdown} N-\overset{S}{\underset{\parallel}{C}}-N\underset{R^8}{\overset{R^7}{\diagdown}} \\ X^- \end{array}$$

wherein: $Y^2$ is an alkyl of 1–24 carbons, aryl of 6–24 carbons, aralkyl of 7 to 25 carbons, the atoms chosen from C, N, O, and S necessary to form a 5- or 6-membered ring or $L^2CR^{14}CH_2$;

$L^2$ is a linking group;
$Y^3$ represents O or S;
$R^6$ is hydrogen, alkyl of 1 to 24 carbons, aryl of 6 to 24 carbons, aralkyl of 7 to 25 carbons or halogen;
$R^7$ and $R^8$ independently represent alkyl of 1–24 carbons, aryl of 6–24 carbons, aralkyl of 7 to 25 carbons or the atoms chosen from C, N, O and S necessary to form a 5- or 6-membered ring or $R^7$ and $R^8$ may be taken together to represent the atoms C, N, O and S necessary to form a 5- or 6-membered ring;
$R^9$ and $R^{10}$ independently represent hydrogen, alkyl of 1 to 24 carbons, nitro, carboxyl, mercapto, —$OR^{12}$, the atoms chosen from C, N, O, and S necessary to form a 5- or 6-membered ring or taken together $R^9$ and $R^{10}$ may represent the atoms chosen from C, N, O, and S necessary to form a 5- or 6-membered ring;
$R^{12}$ represents hydrogen or an alkyl of 1–5 carbons;
$R^{14}$ represents hydrogen or an alkyl of 1–24 carbons;
X- is a counterion;
n is an integer chosen from 0 and 1.

2. The compound recited in claim 1 wherein:
$L^1$ represents a covalent chemical bond, alkyl of 1 to 20 carbons, aryl of 6–24 carbons, or aralkyl of 7 to 25 carbons;
$R^1$ represents hydrogen, alkyl of 1–3 carbons, aryl of 6–10 carbons, or aralkyl of 7–11 carbons;
$R^2$ and $R^3$ independently represent alkyl of 1–6 carbons, aryl of 6–10 carbons, aralkyl of 7–11 carbons, or taken together $R^2$ and $R^3$ may represent the atoms chosen from C, N and O necessary to form a 5- or 6-membered ring;
$R^4$ and $R^5$ independently represent hydrogen or alkyl of 1–4 carbon atoms;
X- is chosen from the set consisting of halide, $ClO_4$—, $BF_4$—, p-$CH_3C_6H_4SO_3$-;
$L^2$ is chosen from the set consisting of a covalent chemical bond, alkyl of 1 to 20 carbons, and aryl of 6–24 carbons;
$R^6$ represents hydrogen, alkyl of 1–3 carbons, aryl of 6–10 carbons, or aralkyl of 7–11 carbons;
$R^7$ and $R^8$ independently represent alkyl of 1–6 carbons, aryl of 6–10 carbons, aralkyl of 7–11 carbons, or taken together $R^7$ and $R^8$ may represent the atoms chosen from C, N and O necessary to form a 5- or 6-membered ring;
$R^9$ and $R^{10}$ independently represent hydrogen or alkyl of 1–4 carbon atoms;
X- is a counterion chosen from the set consisting of halide, $ClO_4$—, $BF_4$—, P-$CH_3C_6H_4SO_3$-.

3. The compound recited in claim 2 wherein:

$L^1$ represents a covalent chemical bond or an alkyl or 1–3 carbons;
$R^1$ represents hydrogen or alkyl of 1–3 carbons;
$R^2$ and $R^3$ represent alkyl of 1–3 carbons, or taken together $R^2$ and $R^3$ may represent the atoms chosen from C, N and O necessary to form a 5- or 6-membered ring;
$L^2$ represents a covalent chemical bond or an alkyl of 1–3 carbons;
$R^6$ represents hydrogen or alkyl of 1–3 carbons;
$R^7$ and $R^8$ represent alkyl of 1–3 carbons, or taken together $R^7$ and $R^8$ may represent the atoms chosen from C, N and O necessary to form a 5- or 6-membered ring.

4. A compound as recited in claim 1 chosen from the set consisting of:

$C_{10}H_{22}-N\underset{Cl^-}{\overset{+}{\diagdown\diagup}}N-\overset{O}{\underset{\parallel}{C}}-N\overset{CH_3}{\underset{CH_3}{\diagdown}}$ ;

$C_{12}H_{25}-\overset{O}{\underset{\parallel}{C}}-N\underset{Cl^-}{\overset{+}{\diagdown\diagup}}N-\overset{O}{\underset{\parallel}{C}}-N\overset{CH_3}{\underset{CH_3}{\diagdown}}$ ;

$CH_3-\overset{O}{\underset{\parallel}{C}}-N\underset{Cl^-}{\overset{+}{\diagdown\diagup}}N-\overset{O}{\underset{\parallel}{C}}-N\overset{CH_3}{\underset{CH_3}{\diagdown}}$ ;

$CH_2=CH-N\underset{Cl^-}{\overset{+}{\diagdown\diagup}}N-\overset{O}{\underset{\parallel}{C}}-N\overset{CH_3}{\underset{CH_3}{\diagdown}}$ ;

$C_6H_5-CH_2-N\underset{Cl^-}{\overset{+}{\diagdown\diagup}}N-\overset{O}{\underset{\parallel}{C}}-N\overset{CH_3}{\underset{CH_3}{\diagdown}}$ ;

$CH_2=CH-CH_2-N\underset{Cl^-}{\overset{+}{\diagdown\diagup}}N-\overset{O}{\underset{\parallel}{C}}-N\overset{CH_3}{\underset{CH_3}{\diagdown}}$ ;

$CH_2=CH-CH_2-N\underset{Cl^-}{\overset{+}{\diagdown\diagup}}N-\overset{O}{\underset{\parallel}{C}}-N\diagdown O$;

$CH_2=CH-N\underset{Cl^-}{\overset{+}{\diagdown\diagup}}N-\overset{S}{\underset{\parallel}{C}}-N\overset{CH_3}{\underset{CH_3}{\diagdown}}$ ;

$CH_2=CH-\overset{O}{\underset{\parallel}{C}}-N\underset{Cl^-}{\overset{+}{\diagdown\diagup}}N-\overset{O}{\underset{\parallel}{C}}-N\overset{CH_3}{\underset{CH_3}{\diagdown}}$ ;

-continued

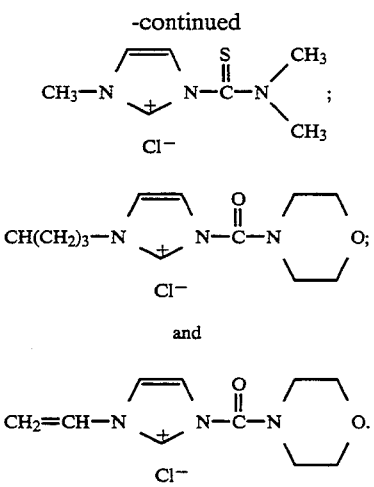

5. A compound chosen from the set consisting of:

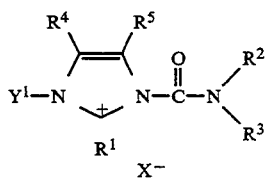

wherein:
$Y^1$ represents an aryl of 1–24 carbons, aralkyl of 7 to 25 carbons, the atoms chosen from C, N, O, and S necessary to form a 5 -or 6-membered ring, or -$L^1CR^{13}CH_2$;
$L^1$ is a linking group;
$R^1$ is hydrogen, alkyl of 1 to 24 carbons, aryl of 6 to 24 carbons, aralkyl of 7 to 25 carbons or halogen;
$R^2$ and $R^3$ independently represent alkyl of 1–24 carbons, aryl of 6–24 carbons, aralkyl of 7 to 25 carbons or $R^2$ and $R^3$ independently may represent, or be taken together to represent the atoms chosen from C, N, O and S necessary to form a 5- or 6-membered ring;
$R^4$ and $R^5$ independently represent hydrogen, alkyl of 1 to 24 carbons, nitro, carboxyl, mercapto, —$OR^{11}$, or the atoms chosen from C, N, O, and S necessary to form a 5- or 6-membered ring or $R^4$ and $R^5$ may be taken together to represent the atoms chosen from C, N, O, and S necessary to form a 5- or 6-membered ring;
$R^{11}$ represents hydrogen or an alkyl of 1–5 carbons;
$R^{13}$ represents hydrogen or an alkyl of 1–24 carbons;
X- is a counterion;
with the proviso that at least one substituent chosen from the set consisting of $Y^1$, $R^1$, $R^2$, $R^3$, $R^4$ and $R^5$ represents an alkyl of 6–24 carbons; and

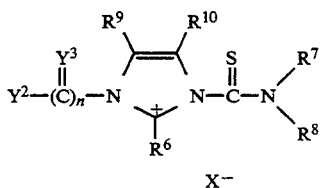

wherein:
$Y_2$ is an alkyl of 1–24 carbons, aryl of 6–24 carbons, aralkyl of 7 to 25 carbons, the atoms chosen from C, N, O, and S necessary to form a 5- or 6-membered ring, $L^2CR^{14}CH_2$;
$L^2$ is a linking group;
$Y_3$ represents O or S;
$R^6$ is hydrogen, alkyl of 1 to 24 carbons, aryl of 6 to 24 carbons, aralkyl of 7 to 25 carbons or halogen;
$R^7$ and $R^8$ independently represent alkyl of 1–24 carbons, aryl of 6–24 carbons, aralkyl of 7 to 25 carbons or the atoms chosen from C, N, O and S necessary to form a 5- or 6-membered ring or $R^7$ and $R^8$ may be taken together to represent the atoms chosen from C, N, O and S necessary to form a 5- or 6-membered ring;
$R^9$ and $R^{10}$ independently represent hydrogen, alkyl of 1 to 24 carbons, nitro, carboxyl, mercapto, —$OR^{12}$, the atoms chosen from C, N, O, and S necessary to form a 5- or 6-membered ring or taken together $R^9$ and $R^{10}$ may represent the atoms chosen from C, N, O, and S necessary to form a 5- or 6-membered ring;
$R^{12}$ represents hydrogen or an alkyl of 1–5 carbons;
$R^{14}$ represents hydrogen or an alkyl of 1–24 carbons;
X- is a counterion;
n is an integer chosen from 0 and 1.
6. The compound recited in claim 5 wherein:
$L^1$ represents a covalent chemical bond, alkyl of 1 to 20 carbons, aryl of 6–24 carbons, or aralkyl of 7 to 25 carbons; $R^1$ represents hydrogen, alkyl of 1–3 carbons, aryl of 6–10 carbons, or aralkyl of 7–11 carbons;
$R^2$ and $R^3$ independently represent alkyl of 1–6 carbons, aryl of 6–10 carbons, aralkyl of 7–11 carbons, or taken together $R^2$ and $R^3$ may represent the atoms chosen from C, N and O necessary to form a 5- or 6-membered ring;
$R^4$ and $R^5$ independently represent hydrogen or alkyl of 1–4 carbon atoms;
X- is chosen from the set consisting of halide, $ClO_4$—, $BF_4$—, p-$CH_3C_6H_4SO_3$-;
$L^2$ is chosen from the set consisting of a covalent chemical bond, alkyl of 1 to 20 carbons, and aryl of 6–24 carbons;
$R^6$ represents hydrogen, alkyl of 1–3 carbons, aryl of 6–10 carbons, or aralkyl of 7–11 carbons;
$R^7$ and $R^8$ independently represent alkyl of 1–6 carbons, aryl of 6–10 carbons, aralkyl of 7–11 carbons, or taken together $R^7$ and $R^8$ may represent the atoms chosen from C, N and O necessary to form a 5- or 6-membered ring;
$R^9$ and $R^{10}$ independently represent hydrogen or alkyl of 1–4 carbon atoms;
X- is a counterion chosen from the set consisting of halide, $ClO_4$—, $BF_4$—, p-$CH_3C_6H_4SO_3$-.
7. The compound recited in claim 6 wherein:
$L^1$ represents a covalent chemical bond or an alkyl or 1–3 carbons;
$R^1$ represents hydrogen or alkyl of 1–3 carbons;
$R^2$ and $R^3$ represent alkyl of 1–3 carbons, or taken together $R^2$ and $R^3$ may represent the atoms chosen from C, N and O necessary to form a 5- or 6-membered ring;
$L^2$ represents a covalent chemical bond or an alkyl of 1–3 carbons;
$R^6$ represents hydrogen or alkyl of 1–3 carbons;
$R^7$ and $R^8$ represent alkyl of 1–3 carbons, or taken together $R^7$ and $R^8$ may represent the atoms chosen from C, N and O necessary to form a 5- or 6-membered ring.

* * * * *